United States Patent [19]

Chen et al.

[11] 4,299,782

[45] Nov. 10, 1981

[54] PHOSPHORUS DERIVATIVES OF 1,3-DIETHANOLUREA

[75] Inventors: Mabel M. M. Chen, Broomall; Stanley R. Sandler, Springfield, both of Pa.

[73] Assignee: Pennwalt Corporation, Philadelphia, Pa.

[21] Appl. No.: 133,297

[22] Filed: Mar. 24, 1980

[51] Int. Cl.³ .................... C07F 9/40; C08G 18/28
[52] U.S. Cl. .................... 260/932; 521/168; 260/938
[58] Field of Search .................. 260/938, 932

[56] References Cited

U.S. PATENT DOCUMENTS

| | | | |
|---|---|---|---|
| 3,763,281 | 10/1973 | Weil | 260/938 |
| 3,920,733 | 11/1975 | Birum | 260/938 |
| 3,939,226 | 2/1976 | Scharf | 260/938 |
| 3,954,860 | 5/1976 | Birum | 260/938 |
| 4,020,679 | 6/1977 | Kotzsch et al. | 260/938 |

FOREIGN PATENT DOCUMENTS 7304498  10/1973  Netherlands ............ 260/938

*Primary Examiner*—Anton H. Sutto

[57] ABSTRACT

This invention relates to novel phosphorus derivatives of 1,3-diethanolurea and certain polymeric reaction products such as polyurethane resins in which they are incorporated.

1 Claim, No Drawings

PHOSPHORUS DERIVATIVES OF 1,3-DIETHANOLUREA

The phosphorus derivatives of this invention are obtained by the reaction of various phosphorus-containing compounds with 1,3-diethanolurea and have the formula:

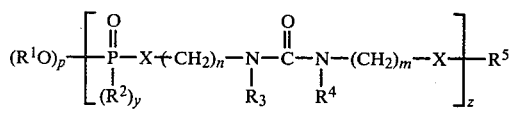

wherein
$R^1$ and $R^2$ are $C_1$ to $C_6$ alkyl, $C_6$ to $C_{10}$ aryl in which the alkyl and aryl groups can be substituted with chlorine or bromine;
n is 1 or 2;
p is 1 or 2;
y is 0 or 1;
m is 0, 1, or 2;
X is oxygen or a covalent bond;
$R^3$ and $R^4$ are, independently, H, —$CH_2CH_2OH$; or

$R_5$ is H or

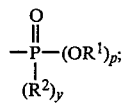

and,
z is 1 to 100.

The aryl radical is preferably phenyl or naphthyl, and most preferably phenyl.

The method of production of polyurethane is well-known and is widely conducted commercially. Briefly, the process involves the reaction of a polyisocyanate with a polyhydroxy compound that may also contain amino, amide, or ester groups. The most common polyurethanes are formed by the reaction of toluene diisocyanate with di- or polyfunctional hydroxy compounds.

It is known that flame retardancy of polyurethanes can be achieved by incorporating phosphorus or halogen compounds in the formulation. Many phosphorus and nitrogen/phosphorus compounds have been disclosed as flame retardants for polyurethane. Most of these are inert additives in that they do not have any reactive group which would permit the compounds to be chemically bound to the polymer chain. Consequently, these compounds have the tendency to migrate to the surfaces of the polymers reducing their overall effectiveness as flame retardants.

Interest has been developing in flame-retardant phosphorus compounds having functional groups which are reactive with the polyol or the polyisocyante used in preparing the polyurethane, and do not have the disadvantage of migrating. Several groups of such compounds are described in U.S. Pat. Nos. 3,297,796; 3,437,607; 3,742,095 and 3,899,453, but are expensive to prepare. Other compounds are such as the phosphoramidates in U.S. Pat. Nos. 3,584,085 and 3,597,503 are hydrolytically less stable. Two other groups of reactive flame retardants for polyurethane are dialkyl N,N-dialkanolaminoalkyl phosphonates, described in U.S. Pat. Nos. 3,076,010 and 3,235,517, and dialkyl N-alkanolaminoalkyl phosphonates described in U.S. Pat. Nos. 3,385,914 and 3,501,421. One member of the dialkyl N,N-dialkanolaminoalkyl phosphonates, diethyl N,N-bis(2-hydroxyethyl)aminoethyl phosphonate is sold commercially. When it is incorporated in the polyurethane formulation, flame retardancy is observed. However, the amount of smoke it generates is unacceptable.

Compared to the above-mentioned compounds, the reactive phosphorus compounds of this invention which contain hydroxyl groups, NH groups, or both are easily prepared from inexpensive starting materials and when incorporated in polyurethanes provide not only effective flame retardancy, but also have the unexpected and important advantage of generating less smoke on combustion.

The composition of this invention can be prepared by the reaction of $C_1$ to $C_6$ alkyl or haloalkyl, or $C_6$ to $C_{10}$ aryl or haloaryl, phosphites, phosphonates, phosphonic dichlorides, or phosphoryl chlorides with diethanolurea at a molar ratio of 1:1 to 2:1. Briefly, the specific phosphorus-containing compound can be heated in a bath at 65°–140° C., preferably 90°–120° C., with diethanol urea, neat or in a solvent. A basic catalyst may be used to promote the reaction between the phosphites or phosphonates and diethanolurea. Suitable catalysts include: the trialkylamines, such as triethylamine; alkali and alkaline earth salts of weak acids, such as sodium methylate. The preferred catalyst is sodium methylate. After the reaction, volatiles, if any, are removed under reduced pressure.

Representative phosphorus compounds that can be used for reaction with diethanolurea are, trialkyl phosphites, such as trimethyl phosphite; trihaloalkyl phosphites, such as tris(2-chloroethyl)-phosphite, tris(2,3-dichloropropyl)phosphite, tris(1,3-dichloropropyl)-phosphite; dialkyl alkyl phosphonates, and substituted dialkyl alkyl phosphonates, such as dimethyl methyl phosphonate, dimethyl hydroxymethyl phosphonate; aryl phosphonic dichlorides, such as phenyl phosphonic dichloride; and dialkyl phosphoryl chlorides, such as dimethyl phosphoryl chloride and diethyl phosphoryl chloride.

Representative compounds of this invention are as follows:

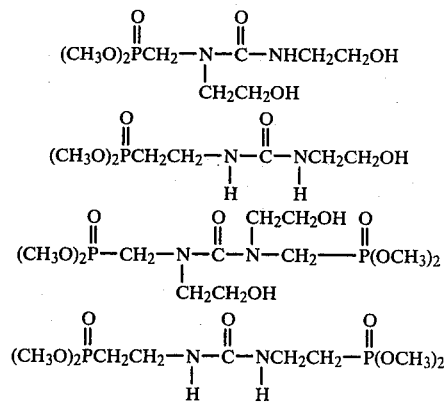

-continued $$CH_3O-\underset{\underset{CH_3}{|}}{\overset{\overset{O}{\|}}{P}}-OCH_2CH_2-\underset{H}{N}-\overset{\overset{O}{\|}}{C}-\underset{H}{N}CH_2CH_2-O-\underset{\underset{CH_3}{|}}{\overset{\overset{O}{\|}}{P}}-OCH_3$$

$$CH_3O\text{-}[\underset{\underset{C_6H_5}{|}}{\overset{\overset{O}{\|}}{P}}-OCH_2CH_2-\underset{H}{N}-\overset{\overset{O}{\|}}{C}-\underset{H}{N}CH_2CH_2-O]_{1-50}H$$

$$CH_3O\text{-}[\underset{\underset{CH_3}{|}}{\overset{\overset{O}{\|}}{P}}-OCH_2CH_2-\underset{H}{N}-\overset{\overset{O}{\|}}{C}-\underset{H}{N}CH_2CH_2-O]_{50-100}H$$

wherein
n is 1–5
A is Cl or Br

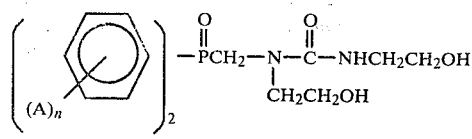

wherein
n is 1–5
A is Cl or Br $$(CCl_3CH_2CH_2CH_2O)_2-\overset{\overset{O}{\|}}{P}OCH_2CH_2-NH-\overset{\overset{O}{\|}}{C}-NHCH_2CH_2O-\overset{\overset{O}{\|}}{P}(OCH_2CH_2CH_2CCl_3)_2$$

$$(\underset{\underset{Cl}{|}}{CH_2}-\underset{\underset{Cl}{|}}{CHCH_2O})_2\overset{\overset{O}{\|}}{P}OCH_2CH_2-NH\overset{\overset{O}{\|}}{C}-NHCH_2CH_2-OP(OCH_2-\underset{\underset{Cl}{|}}{CH}-\underset{\underset{Cl}{|}}{CH_2})_2$$

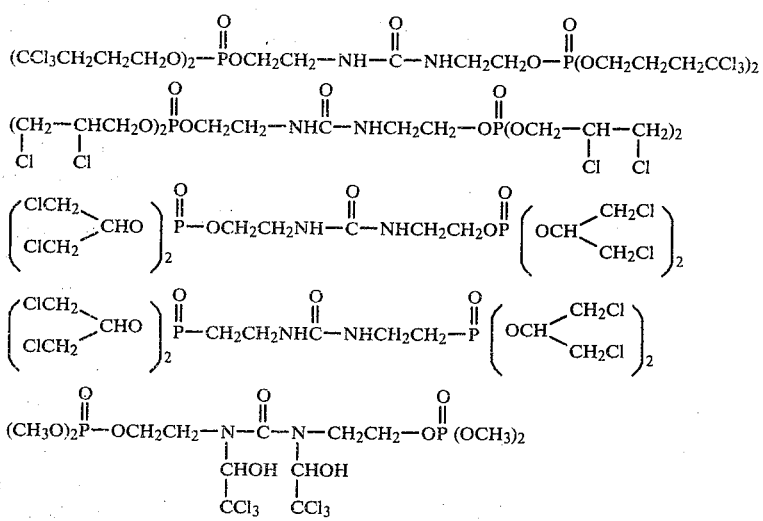

$$(CH_3O)_2\overset{\overset{O}{\|}}{P}-OCH_2CH_2-\underset{\underset{\underset{CCl_3}{|}}{CHOH}}{N}-\overset{\overset{O}{\|}}{C}-\underset{\underset{\underset{CCl_3}{|}}{CHOH}}{N}-CH_2CH_2-\overset{\overset{O}{\|}}{OP}(OCH_3)_2$$

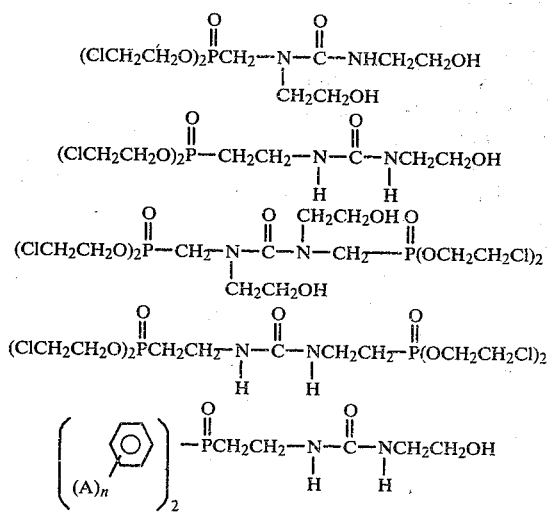

The phosphorus derivatives of diethanolurea of this invention can also be used to impart flame retardancy to a variety of substances besides polyurethane; for example, textile, polyvinyl chloride, polystyrene, polyester resin, paper, wood, and leather. These compounds may also be useful as flame retardant plasticizers for various polymers in particular PVC and other halogenated resins. The compounds with available hydroxyl groups can be used as intermediates to prepare other organic compounds. The compositions of this invention can also be used as crosslinking agents for urethane foams.

For use in flame retarding polyurethane resins, the preferred diethanolurea phosphorus derivatives are those prepared from trialkyl phosphites and dialkyl hydroxyalkyl phosphonates.

The preferred compounds of this invention are as follows:

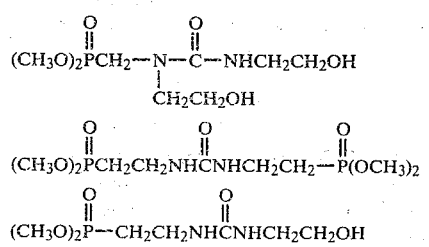

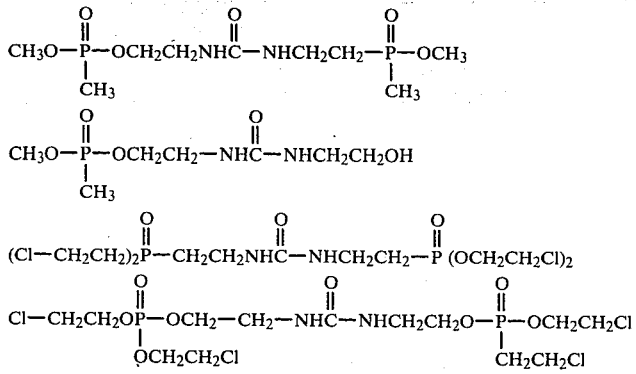

The compounds of this invention are generally clear, almost colorless, viscous liquids. They usually are added to urethane resins in the amount of 5 to 40 percent, by weight based on the weight of the total composition to provide 1 to 4 percent phosphorus content for imparting flame retardancy. However, the foregoing ranges are merely preferred as offering both acceptable flame retardancy and good physical properties of the polyurethane. Thus, higher or lower amounts of the compounds of this invention can also be used.

In the Examples below, the polyurethane resins are evaluated for flame retardancy using ASTM D-1692-74, and for smoke produced on combusion using an NBS Smoke Chamber according to ASTM Special Technical Publication 422 (1969) and NFPA-258-T. These Examples illustrate the invention are not to be taken as a limitation thereof.

EXAMPLE 1

A mixture of 132.0 g (0.94 mole) of dimethyl hydroxymethyl phosphonate and 139.5 g (0.94 mole) of 1,3-diethanolurea is stirred with heating at 90°–95° C. for 4 hours. Water is removed under reduced pressure. The light-colored clean syrup weighs 228.0 g. The resulting compound is analyzed to contain 11.1% phosphorus and 11.8% nitrogen. The analysis is consistent with the structure of this compound as:

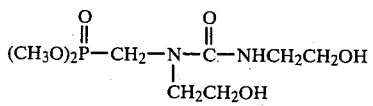

EXAMPLE 2

Trimethyl phosphite, 148.8 g (1.2 moles), 1,3-diethanolurea, 74.0 g (0.5 mole), and sodium methylate, 3.0 g, are heated with stirring in a 500 ml 3-neck flask fitted with a mechanical stirrer, and a distilling head attached to a condenser. Temperature of the oil bath is kept around 110° C. The distillate is collected in fractions and analyzed by gas chromatography for the presence of methanol. The reaction is discontinued when no more methanol is distilled over. The product is obtained as a light-colored syrupy oil and weighs 137.4 g. The resulting compound on analysis is found to contain 33.2% carbon, 7.22% hydrogen, 10.0% nitrogen, and 16.3% phosphorus. The analysis is consistent with the structure of this compound as:

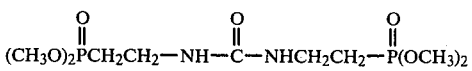

but does not preclude that some

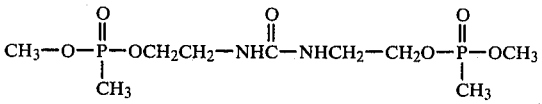

may be present.

EXAMPLE 3

Trimethyl phosphite, 38.2 g (0.308 mole), 1,3-diethanolurea, 38.0 g (0.25 mole), and sodium methylate, 1.0 g are heated with stirring in a 500 ml 3-neck flask fitted with a mechanical stirrer and a distilling-head attached to a condenser. Temperature of the oil bath is kept below 120° C. The distillate is collected in fractions and analyzed by gas chromatography for the presence of methanol. The reaction is discontinued when no more methanol is distilled over. After evaporation of volatiles under vacuum, the product, a light-colored syrupy oil, weighs 60.2 g. The resulting compound on analysis is found to contain 33.0% carbon, 7.11% hydrogen, 11.1% nitrogen, and 14.9% phosphorus. The analysis is consistent with the structure of the compound as:

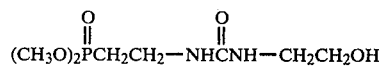

but does not preclude that some

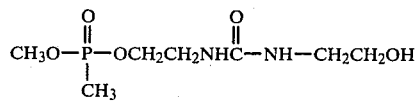

may be present.

EXAMPLE 4

A foam-forming polyurethane formulation is prepared from the following ingredients in the indicated proportions:

| Ingredients | Parts by weight, gms |
| --- | --- |
| Polyether polyol[1] | 100.0 |

| Ingredients | Parts by weight, gms |
|---|---|
| Silicone Surfactant[2] | 1.0 |
| Catalyst[3] | 3.0 |
| Distilled water | 0.9 |
| Fluorocarbon blowein agent[4] | 50.0 |
| Polymethylene polyphenylisocyanate[5] (Index 110) | 203.0 |
| Compound of Example 1 | 40.0 |
| Total | 397.9 |

Notes:
[1]Poly G-71-530 (Olin)
[2]DC-193 (Dow Corning)
[3]Penncat 283 (Pennwalt)
[4]Isotron 11 (Pennwalt)
[5]PAPI (Upjohn)

All of the above ingredients, with the exception of the catalyst and the isocyanate, are first blended together. Then the catalyst is added. After stirring thoroughly, the isocyanate is blended in, and the mixture, stirred with a high-speed stirrer for 10-20 seconds, is allowed to expand into a rigid foam. Test results of this foam are listed in Table 1.

EXAMPLE 5

The procedure of Example 4 is followed except that in order to demonstrate the advantage of the flame-retardant compounds of this invention over prior art, 39.0 g of diethyl N,N-bis(2-hydroxyethyl)aminomethyl phosphonate (a commercially available flame-retardant) is used in place of the flame-retardant of Example 1. Test results are listed in Table 1.

EXAMPLE 6

The procedure of Example 4 is followed except 21.0 g of the flame-retardant compound of Example 2 is used and the amount of polymethylene polyphenyl isocyanate is lowered to 159.0. Test results are listed in Table 1.

EXAMPLE 7

The procedure of Example 4 is followed except that 34.0 g of the flame-retardant compound of Example 3 is substituted and the amount of polymethylene polyphenylisocyanate is reduced to 180.0 g. Test results are listed in Table 1.

EXAMPLE 8

The flame retardance of the foams of Examples 4-7 tested according to ASTM D-1692-74 using a sample of 6×2 0.5 inch. It is found that all foams in Examples 4-7 were self-extinguishing. The extent of burn, when the flame became extinguished, is measured in inches. All results in Table 1 are the averages of 3 values. For smoke density measurement, a foam sample of 3×3×1-inch is burned in an Aminco NBS Smoke Chamber using the method described in ASTM Special Technical Publication 422 (1969) and NFPA-258-T "Smoke Generated by Solid Materials", May 1974, using the flame mode of operation. The maximum specific optical smoke density, calculated as the $D_{mc}$, the maximum corrected specific optical density, per gram of foam sample, is calculated as the average of 2 values.

TABLE 1

| Foam Sample | Flame Retardant (FR) Used | % P | % Wt. Add-on of FR | ASTM D-1692-74 Extent of Burn (Inches) | Max. Specific Optical Smoke Density ($D_{mc}$/g sample) |
|---|---|---|---|---|---|
| Example 4 | Example 1 | 1.37 | 11.5 | 1.10 | 80.7 |
| Example 5 | Prior Art* | 1.37 | 11.1 | 1.26 | 86.4 |
| Example 6 | Example 2 | 1.37 | 7.4 | 0.931 | 57.1 |
| Example 7 | Example 3 | 1.37 | 10.6 | 0.945 | 68.3 |

*PRIOR ART FLAME RETARDANT is diethyl N,N-bis-(2-hydroxyethyl) aminomethyl phosphonate.

As seen from the data in Table 1, with equal percentage of phosphorus in the formulation of rigid polyurethane, foams containing the novel compositions of this invention surprisingly not only have better flame retardancy, but also generate less smoke (per gram of sample) than foams containing the commercially available phosphorus-based flame retardant of Example 5, diethyl N,N-bis(2-hydroxyethyl)aminomethyl phosphonate.

EXAMPLE 9

Tris(2-chloroethyl)phosphite, 269.5 g (1.0 mole) and diethanolurea, 74.0 g (0.5 mole), and sodium methylate, 3.0 g are reacted at 100° C. for 5-6 hours. The reaction mixture was stripped of volatiles at reduced pressure and a light viscous oil was obtained weighing 270.0 g. The analysis is consistent with the formula of this compound as

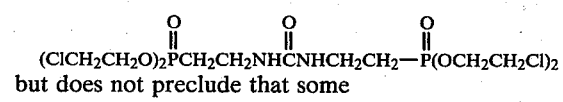

but does not preclude that some

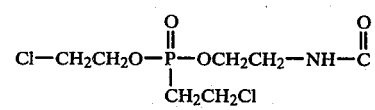

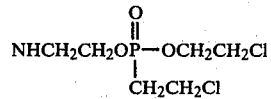

may be present.

This compound, when used in place of the commercial flame-retardant 5, gives flame retardant, low smoke polyurethane resin.

We claim:
1. A compound useful as a flame retardant for polyurethane resins, comprising:
A compound having a formula selected from the group consisting of

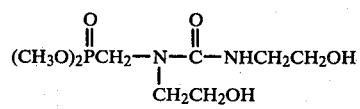

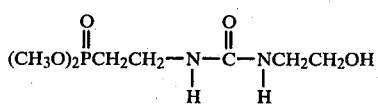

and

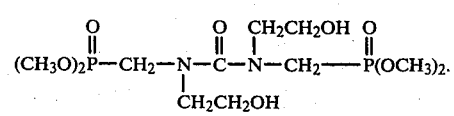

* * * * *